United States Patent
Wang et al.

(10) Patent No.: US 10,165,992 B2
(45) Date of Patent: Jan. 1, 2019

(54) X-RAY IMAGING SYSTEMS AND DEVICES

(71) Applicant: Carestream Health, Inc., Rochester, NY (US)

(72) Inventors: Xiaohui Wang, Pittsford, NY (US); Michael D. Heath, Rochester, NY (US); David H. Foos, Webster, NY (US); James H. Ogle, Jr., Birmingham, AL (US)

(73) Assignee: Carestream Health, Inc., Rochester, NY (US)

( * ) Notice: Subject to any disclaimer, the term of this patent is extended or adjusted under 35 U.S.C. 154(b) by 126 days.

(21) Appl. No.: 14/974,370

(22) Filed: Dec. 18, 2015

(65) Prior Publication Data

US 2016/0181053 A1    Jun. 23, 2016

Related U.S. Application Data

(60) Provisional application No. 62/093,443, filed on Dec. 18, 2014.

(51) Int. Cl.
*H01J 35/00* (2006.01)
*A61B 6/00* (2006.01)
(Continued)

(52) U.S. Cl.
CPC ............ *A61B 6/4007* (2013.01); *A61B 6/022* (2013.01); *A61B 6/0492* (2013.01); *A61B 6/06* (2013.01);
(Continued)

(58) Field of Classification Search
CPC .. A61B 6/08; A61B 6/06; A61B 6/587; A61B 6/4405; A61B 6/506; A61B 6/588;
(Continued)

(56) References Cited

U.S. PATENT DOCUMENTS

| | | | |
|---|---|---|---|
| 2,041,242 A | 5/1936 | Goldfield | |
| 4,017,858 A | 4/1977 | Kuipers | |

(Continued)

FOREIGN PATENT DOCUMENTS

| | | |
|---|---|---|
| JP | 04-164437 | 6/1992 |
| JP | 2000-023955 | 1/2000 |
| WO | 90/14748 | 11/1990 |

OTHER PUBLICATIONS

A. Reyes-Mena et al., Miniature X-Ray Tubes Utilizing Carbon-Nanotube-Based Cold Cathoses, International Centre for Diffraction Data, Advances in X-ray Analysis, 2005, vol. 48, pp. 204-209.
(Continued)

*Primary Examiner* — Irakli Kiknadze

(57) ABSTRACT

An x-ray imaging system, such as a mobile radiography unit, includes a plurality of stationary carbon nanotube based x-ray sources to be selectively energized. A circuit enables a selected subset of the radiation sources to be energized while another subset may be disabled. A light source may be attached to the support arm of the mobile radiography unit and a source of electric power is configured to energize the light source upon operator contact with the unit. The plurality of stationary x-ray sources may be used to capture a plurality of 2-D projection images of a subject to reconstruct a 3-D image thereof. The 3-D image is used to generate a 2-D projection image of the subject.

20 Claims, 7 Drawing Sheets

(51) Int. Cl.
*G01N 23/04* (2018.01)
*H05G 1/56* (2006.01)
*A61B 6/06* (2006.01)
*A61B 6/02* (2006.01)
*A61B 6/10* (2006.01)
*A61B 6/04* (2006.01)
*H05G 1/70* (2006.01)

(52) U.S. Cl.
CPC ............ *A61B 6/105* (2013.01); *A61B 6/4405* (2013.01); *A61B 6/467* (2013.01); *A61B 6/5211* (2013.01); *A61B 6/58* (2013.01); *A61B 6/4291* (2013.01); *H01J 2201/30469* (2013.01); *H01J 2235/062* (2013.01); *H01J 2235/068* (2013.01); *H05G 1/70* (2013.01)

(58) Field of Classification Search
CPC ....... A61B 6/508; A61B 6/4291; A61B 6/542; A61B 6/547; A61B 6/4266; A61B 6/4208; A61B 6/4233; A61B 6/4283; A61B 6/461; A61B 6/583; A61B 6/4411; A61B 6/46; A61B 6/0492; A61B 6/105; A61B 6/4007; A61B 6/467; A61B 6/5211; A61B 6/58; A61B 17/068; A61B 2017/07271; A61B 2017/07285; A61B 2017/2923; A61B 17/320016; A61B 2017/00017; A61B 6/032; A61B 6/4028; A61B 6/022; A61B 6/04; A61B 6/025; A61B 6/5205; A61B 6/487; A61B 6/54; A61B 6/4014; A61B 6/548; A61B 6/502; A61B 6/035; A61B 6/107; A61B 6/145; A61B 17/07207; A61B 17/00398; A61B 17/00734; A61B 2017/07278; A61B 17/2927; A61B 2017/320052; A61B 17/1155; A61B 6/405; A61B 6/482; A61B 6/00; A61B 6/14; A61B 6/4035; A61B 6/4241; H01J 2201/30469; H01J 2235/062; H01J 2235/068; H01J 35/065; H01J 2235/064; H01J 35/14; H01J 35/22; H05G 1/70; H05G 1/10; H05G 1/32; H05G 1/56; H05G 1/08; H05G 1/34; H05G 1/54; H05G 1/20; H05G 1/265; H05G 1/52; H05G 1/58; H05G 1/06; H05G 1/26
USPC .............. 378/62, 193–198, 205, 206, 9, 119
See application file for complete search history.

(56) References Cited

U.S. PATENT DOCUMENTS

| | | | |
|---|---|---|---|
| 4,246,486 A | 1/1981 | Madsen | |
| 4,341,279 A | 7/1982 | Waerve | |
| 4,387,468 A | 6/1983 | Fenne et al. | |
| 4,716,581 A | 12/1987 | Barud | |
| 4,752,948 A | 6/1988 | MacMahon | |
| 4,836,671 A | 6/1989 | Bautista | |
| 5,067,145 A | 11/1991 | Siczek et al. | |
| 5,241,578 A | 8/1993 | MacMahon | |
| 5,388,143 A | 2/1995 | MacMahon | |
| 5,475,730 A | 12/1995 | Galando | |
| 5,499,284 A | 3/1996 | Pelligrino et al. | |
| 5,539,798 A | 7/1996 | Asahina et al. | |
| 5,550,889 A | 8/1996 | Gard et al. | |
| 5,617,462 A | 4/1997 | Spratt | |
| 5,751,783 A | 5/1998 | Granfors et al. | |
| 5,844,961 A | 12/1998 | McEvoy et al. | |
| 5,949,811 A | 9/1999 | Baba et al. | |
| 6,047,042 A | 4/2000 | Khutoryansky et al. | |
| 6,154,522 A | 11/2000 | Cumings | |
| 6,192,105 B1 | 2/2001 | Hunter et al. | |
| 6,193,415 B1 | 2/2001 | Kadowaki et al. | |
| 6,208,710 B1 | 3/2001 | Nagai | |
| 6,327,336 B1 | 12/2001 | Gingold et al. | |
| 6,404,851 B1 | 6/2002 | Possin et al. | |
| 6,422,750 B1 | 7/2002 | Kwasnick et al. | |
| 6,491,430 B1 | 12/2002 | Scissler | |
| 6,702,459 B2 | 3/2004 | Barnes et al. | |
| 6,760,405 B2 | 7/2004 | Ruetten et al. | |
| 6,851,853 B2 | 2/2005 | Nakagawa et al. | |
| 6,895,268 B1 | 5/2005 | Rahn et al. | |
| 6,942,385 B2 | 9/2005 | Fadler et al. | |
| 6,944,266 B2 | 9/2005 | Yamazaki et al. | |
| 6,950,492 B2 | 9/2005 | Besson | |
| 7,010,091 B2 | 3/2006 | Hayashida et al. | |
| 7,016,467 B2 | 3/2006 | Brooks | |
| 7,120,229 B2 | 10/2006 | Takasawa | |
| 7,156,553 B2 | 1/2007 | Tanaka et al. | |
| 7,211,802 B1 | 5/2007 | Dhurjaty et al. | |
| 7,345,274 B2 | 3/2008 | Nilsson | |
| 7,368,724 B2 | 5/2008 | Morii et al. | |
| 7,490,986 B2 | 2/2009 | Takekoshi et al. | |
| 7,495,226 B2 | 2/2009 | Jadrich et al. | |
| 7,519,155 B2 | 4/2009 | Mollus et al. | |
| 7,581,884 B1 | 9/2009 | Barnes et al. | |
| 7,601,961 B2 | 10/2009 | Franklin et al. | |
| 7,611,282 B2 | 11/2009 | Koren et al. | |
| 7,613,276 B2 | 11/2009 | Sendai | |
| 7,632,016 B1 | 12/2009 | Huang et al. | |
| 7,744,279 B2 | 6/2010 | Health et al. | |
| 7,780,350 B2 | 8/2010 | Tranchant et al. | |
| 7,794,144 B2 | 9/2010 | Windt | |
| 7,798,710 B1 | 9/2010 | Barnes et al. | |
| 2002/0094064 A1* | 7/2002 | Zhou | A61B 6/032 378/122 |
| 2002/0150215 A1 | 10/2002 | Barnes et al. | |
| 2002/0188194 A1 | 12/2002 | Cosman | |
| 2003/0165216 A1 | 9/2003 | Walker et al. | |
| 2004/0101100 A1 | 5/2004 | Morii et al. | |
| 2005/0058244 A1 | 3/2005 | Tanaka et al. | |
| 2005/0169425 A1 | 8/2005 | Takasawa | |
| 2006/0109958 A1 | 5/2006 | Ertel et al. | |
| 2006/0269114 A1 | 11/2006 | Metz | |
| 2007/0244388 A1 | 10/2007 | Sato et al. | |
| 2007/0255087 A1 | 11/2007 | Minai | |
| 2007/0297569 A1 | 12/2007 | Saunders | |
| 2008/0130837 A1 | 6/2008 | Heath et al. | |
| 2008/0198968 A1 | 8/2008 | Takekoshi et al. | |
| 2008/0204012 A1 | 8/2008 | Krueger et al. | |
| 2008/0240346 A1 | 10/2008 | Kashiwagi et al. | |
| 2009/0060145 A1 | 3/2009 | Tranchant et al. | |
| 2009/0086889 A1* | 4/2009 | Hashemi | A61B 6/025 378/22 |
| 2009/0136000 A1 | 5/2009 | Nishii et al. | |
| 2009/0180590 A1 | 7/2009 | Borgmann et al. | |
| 2010/0002831 A1 | 1/2010 | Maack | |
| 2010/0322498 A1* | 12/2010 | Wieczorek | A61B 6/032 382/131 |
| 2011/0026667 A1* | 2/2011 | Poorter | A61B 6/025 378/12 |
| 2011/0280367 A1* | 11/2011 | Baeumer | A61B 6/032 378/9 |
| 2012/0039447 A1* | 2/2012 | Lalena | A61B 6/08 378/206 |
| 2014/0093032 A1* | 4/2014 | Dennerlein | A61B 6/025 378/27 |
| 2014/0211917 A1* | 7/2014 | Chen | A61B 6/032 378/62 |
| 2015/0146863 A1* | 5/2015 | Kim | A61B 6/4266 378/91 |

OTHER PUBLICATIONS

P. Sarrazin et al., Carbon-Nanotube Field Emission X-Ray Tube for Space Exploration XRD/XRF Instrument, International Centre for Diffraction Data, Advances in X-ray Analysis, vol. 47, 2004, pp. 232-239.

(56) References Cited

OTHER PUBLICATIONS

Supplementary European Search Report, completed Mar. 5, 2014 for European Patent Application No. 11 76 9395.2, 2 pages.
International Search Report for International application No. PCT/US2011/032035, dated Dec. 19, 2011, 2 pages.
International Search Report for International application No. PCT/US2011/032020, dated Nov. 22, 2011, 2 pages.
International Search Report for International application No. PCT/US2012/0262212, dated Aug. 30, 2012, 2 pages.
Brochure for EasyPos dental x-ray positioning system from website, Mar. 2010, 010.hyphendev.fr file PubEasypos08v3.pdf, 2 pages.
Supplementary Partial European Search Report, for European application No. 11 76 9406, dated Apr. 2014, 1 page.

* cited by examiner

X-RAY IMAGING SYSTEMS AND DEVICES

CROSS REFERENCE TO RELATED APPLICATIONS

This application claims priority to U.S. Patent Application Ser. No. 62/093,443, filed Dec. 18, 2014, in the name of Wang, et al., and entitled IMPROVED X-RAY IMAGING SYSTEMS AND DEVICES.

This application is related in certain respects to U.S. patent application Ser. No. 13/083,860, filed Apr. 11, 2011, in the name of Lalena, et al., and entitled TUBE ALIGNMENT FOR MOBILE RADIOGRAPHY SYSTEM; U.S. patent application Ser. No. 13/284,218, filed Oct. 28, 2011, in the name of Lalena, et al., and entitled PROJECTOR AS COLLIMATOR LIGHT; U.S. patent application Ser. No. 12/906,192, filed Oct. 18, 2010, in the name of Wendlandt, et al., and entitled MOBILE RADIOGRAPHY UNIT HAVING COLLAPSIBLE SUPPORT COLUMN; PCT Patent Application PCT/US15/56644 filed Oct. 21, 2015, in the name of Ficarra, et al., and entitled MOBILE RADIOGRAPHIC IMAGING APPARATUS; and U.S. Patent Application Ser. No. 62/067,083, filed Oct. 22, 2014, in the name of Ficarra, et al., and entitled PATIENT IMPACT AVOIDANCE SYSTEM, all five of which are incorporated herein by reference in their entirety.

FIELD OF THE INVENTION

The subject matter disclosed herein relates to improvements in radiographic imaging systems and devices. In particular, the improvements include carbon nano tube (CNT) based x-ray source arrays used to reconstruct a projection radiographic image, CNT based x-ray source arrays with redundant cathodes and anodes, and an automatic activation of a collimator light source or other component of the radiographic imaging system.

BACKGROUND OF THE INVENTION

X-ray sources utilizing CNTs as a cathode which emit electrons when exposed to an electrical field may be manufactured as an array of x-ray sources. These sources may be positioned to scan a subject and generate images from each x-ray source to be reconstructed using software to provide a 3-D image of the subject faster than using conventional x-ray systems. It would be helpful to use the array of x-ray sources to generate a projection view radiographic image. The CNT x-ray sources are lighter, smaller, work faster, operate at cooler temperatures, and use less peak power than the conventional systems.

CNT based source arrays may be expensive. Their life time depends on the life of the cathodes and anodes. The CNT material on the cathode and the anode surface (tungsten) will degrade over time. It would be advantageous to manufacture a CNT source array that does not require extensive repair or replacement procedures when a CNT source ages or is otherwise degraded.

When making collimation adjustments, with regard to CNT based x-ray systems or conventional systems, the collimator light is turned on by an operator using a dedicated collimator light button or switch. The operator then adjusts the collimation field size by, for example, manipulating knobs that control the radiation field size in radial, or x and y, dimensions. Operator workflow would be improved by reducing requirements for the operator to activate the collimator light by manipulating buttons or switches.

The discussion above is merely provided for general background information and is not intended to be used as an aid in determining the scope of the claimed subject matter.

BRIEF DESCRIPTION OF THE INVENTION

A tomosynthesis x-ray imaging system may be built with an array of stationary x-ray sources, such as CNT sources, arranged in a 2D layout, such as circle, octagon, square, or other arrangement, in order to achieve isotropic spatial resolution in the reconstructed coronal image slices. Such sources may be arranged with a central opening to allow the coexistence of a standard output x-ray tube for standard radiographic imaging. This may be useful if each stationary CNT x-ray source in a tomosynthesis imaging system has limited x-ray output power. The reconstructed tomosynthesis images may be used to create digitally synthesized projection radiographs. The software may also reconstruct a projection view from the 3-D image.

Furthermore, since CNT based cathodes can be built with high density, similar to LEDs in some respects, redundant (or back up) cathodes/anodes, a subset of the total, can be built inside the x-ray source array during manufacturing, then turned on when the initial (primary) cathodes/anodes reach a certain life time and/or their performance degrades to unacceptable levels.

Any time the operator adjusts the collimation field size by turning or touching the field adjustment controls, the collimator light is automatically turned on for a predetermined period of time, which eliminates the need for the operator to press or switch the collimator light control button. The collimator activation button/switch may be integrated into the field adjustment knobs, for example, by making them either touch sensitive or motion sensitive.

In one embodiment, an x-ray tube head uses a plurality of carbon nanotubes each capable of emitting x-rays when energized by an electric current. A circuit enables a selected subset of the radiation sources to be switchably connected to a source of electric current, and for selectively disabling a second subset of the radiation sources from being switchably connected to the source of electric current. A switch circuit switchably connects the selected ones of the enabled radiation sources in the first subset to the source of electric current.

In another embodiment, an x-ray imaging system uses a source of x-ray radiation attached to a tube head at one end of a movable support arm. A light source is attached to the support arm, and a source of electric power is configured to energize the light source. The source of electric power is configured to be switchably connected to the light source in response to an action performed by an operator of the x-ray imaging system.

In another embodiment, a projection x-ray imaging system uses a plurality of stationary x-ray sources each fixed at a different angle with respect to a subject to be imaged. A series of 2-D projection image of the subject may be captured at the corresponding different angle. A processing system receives the plurality of 2-D x-ray images of the subject and reconstructs a 3-D image of the subject. The 3-D image is used to generate a 2-D projection image of the subject.

The summary descriptions above are not meant to describe individual separate embodiments whose elements are not interchangeable. In fact, many of the elements described as related to a particular embodiment can be used together with, and possibly interchanged with, elements of other described embodiments. Many changes and modifications may be made within the scope of the present invention without departing from the spirit thereof, and the invention includes all such modifications. The drawings below are intended to be drawn neither to any precise scale with respect to relative size, angular relationship, relative position, or timing relationship, nor to any combinational relationship with respect to interchangeability, substitution, or representation of a required implementation.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is further provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which.

DETAILED DESCRIPTION OF THE INVENTION

Figure 1:
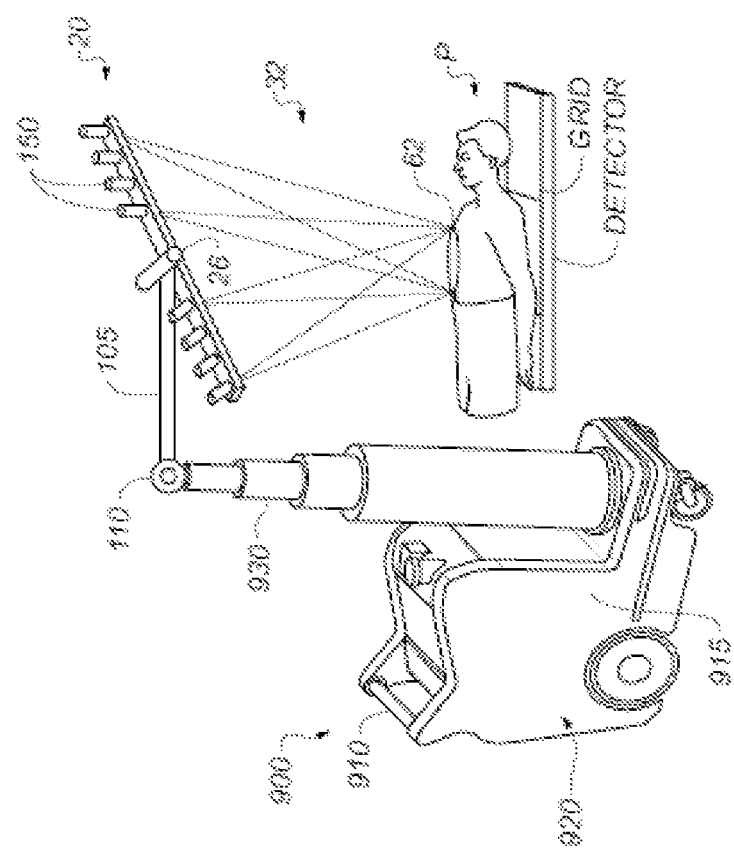
FIG. 1 shows an exemplary mobile x-ray system.

Referring to FIGS. 1-4, there are illustrated embodiments of a tube head assembly 20 having x-ray sources 150 emitting x-rays 32 that expose a radiation field 62 on a subject P to be imaged. The tube head assemblies may be rotatably attached to one end of an adjustable support arm 105, which is configured to be adjustably movable by an operator in three dimensions. The radiation field 62 may have its dimensions controlled by adjustment of one or more collimator blades 402. A light source 26 may project visible light onto the radiation field to coincide with the x-rays 32 of the x-ray source 150 and illuminate the projected radiation field 62 on the subject P with visible light prior to exposing the subject P. The support arm 105 may be configured to switch on the light source upon detecting physical contact from an operator. Alternatively, the tube head may include a sensor 202 that detects movement of the tube head 20 and, in response, activates the light source 26. A joint 110 in the support arm 105 may sense a movement of the joint to trigger activation of the light source 26. In other embodiments, with respect to the light source 26 attached to the x-ray source assembly 20, or tube head, the light source 26 moves together with the x-ray source assembly as it is manipulated into an imaging position by an operator. A source of electric power configured to energize the light source may be electrically activated such that power is automatically provided to the light source in response to an action performed by an operator of the mobile or stationary x-ray imaging system. Such a feature may obviate the need for an operator to separately activate the light source 26 such as by pressing a button or activating a dedicated switched circuit. The action performed by the operator to automatically activate the light source may include physically contacting knobs to adjust the collimator without requiring the operator to activate a dedicated switch for powering the light source. The action performed by the operator may also include disengaging a brake or lock that is used to constrain movement of the x-ray source assembly which movement is detected by the x-ray system and causes an automatic activation of the light source. Other actions performed by the operator and detectable by the radiographic system for activating the light source or other electrically powered components of the radiography system may include grasping a handle on the tube head, touching any portion of a support arm or tube head, including a button, knob, touch screen display, or a burn guard. Such contact may be detected by a capacitively coupled activation circuit in electrical (capacitive) communication with surfaces of the radiography apparatus, which surfaces may be electrically conductive or non-conductive. Other sensors may detect the operator approaching the imaging system or moving a part of the imaging system, such as a mechanical joint in a support arm. Such sensors or detectors in the radiography system may include infra-red movement detectors set to detect movement within a short distance from the imaging system, an ultrasound detector set to detect an object in close proximity to the detector, a contact detector set to detect contact on a surface of the tube head or support arm, a motor control device to detect movement of a mechanical joint in the tube head or support arm, an electromagnetic proximity detector set to detect movement within a short distance from the imaging system, an accelerometer to detect movement of the tube head or support arm, or another device such as a hand held switch used to activate the radiation source, a Bluetooth transceiver to detect an operator in proximity to the detector who is carrying a complementary Bluetooth transceiver. The light source 26 may be adjustable to project light to form a visible illuminated area on the subject P of a size that is greater than, less than, or equal to the area of the radiation field 62.

Figure 4:
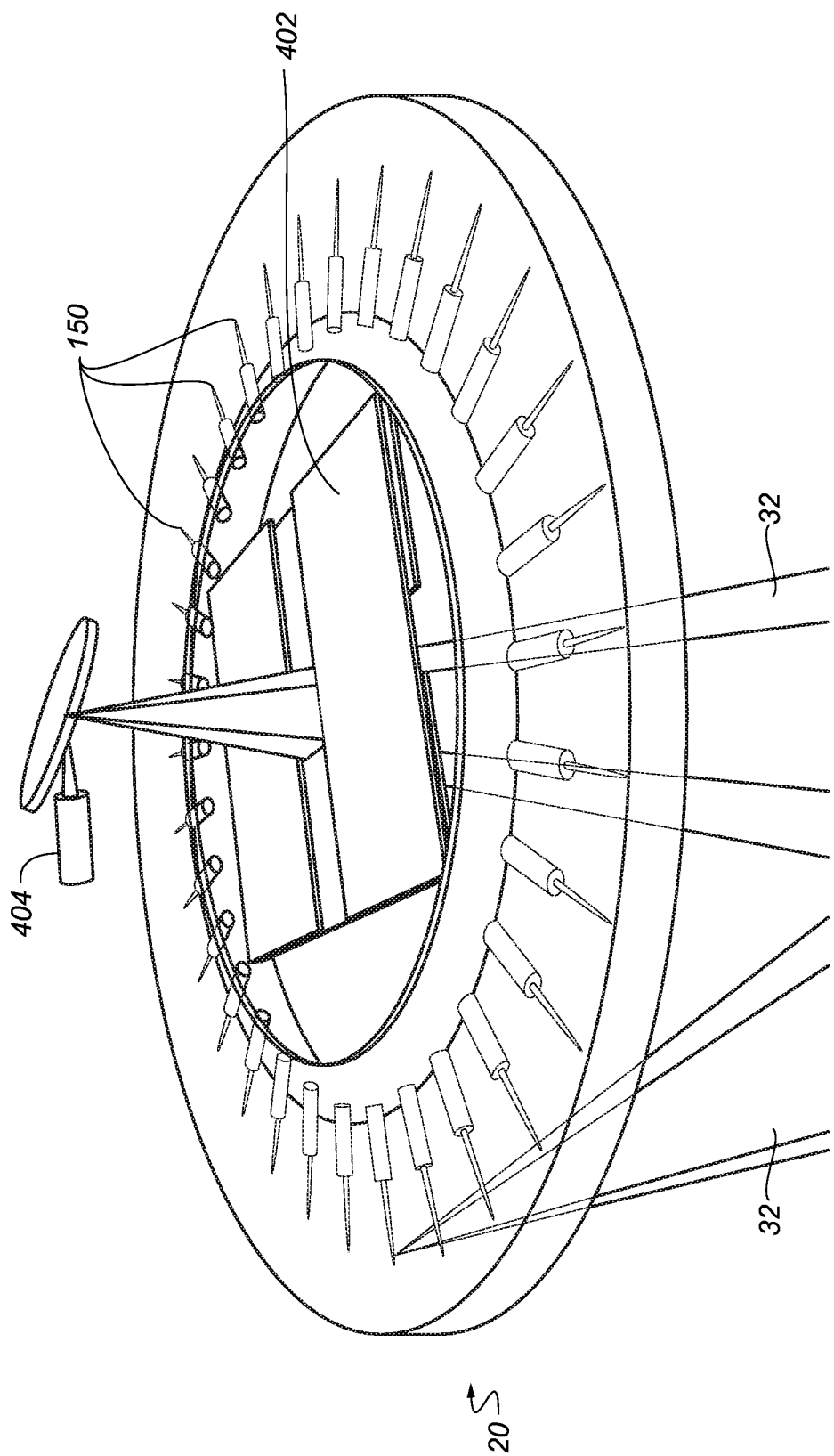
FIG. 4 illustrates another view of the tube head assembly of FIG. 3.

As shown in FIG. 4, collimator blades 402 may be used to shape the output radiation beam and collimator light by blocking a portion of the emitted radiation or light. It should also be noted that some collimator arrangements use a single blade, rather than having multiple blades 402 as shown in FIG. 4, while other collimator embodiments may control a radial opening size of a substantially circular collimator opening. Display of the illuminated radiation field is also of value for making collimator adjustments that reduce backscatter of the x-rays.

The mobile radiography unit of FIG. 1 can provide a tomosynthesis imaging capability according to embodiments of the present invention. As shown in FIG. 1, an embodiment of a mobile radiographic or tomosynthesis system 900 is shown that can include a movable transport frame 920. Mounted to the moveable transport frame 920 can be a support column that supports an x-ray source assembly 20. As shown in FIG. 1, a support column 930 can include a second section 105 that extends outward a fixed/variable distance from a first section 930, where the second section 105 is configured to move (e.g., ride vertically) up and down the first section 930 to the desired height for obtaining the projection images. The system also includes a digital x-ray detector that is wirelessly (e.g., or wired, tethered) connected to a system controller 915 contained inside the moveable transport frame 920. The system controller 915 can implement and/or control the functionality of the mobile radiographic/tomosynthesis system 900 (e.g., functionality provided through a console or control display 910). The system controller 915 can be provided though one or more of a conventional general purpose processor, digital computer, microprocessor, RISC processor, signal processor, CPU, arithmetic logic unit (ALU), video digital signal processor (VDSP) and/or similar computational machines, programmed accordingly.

Figure 2:
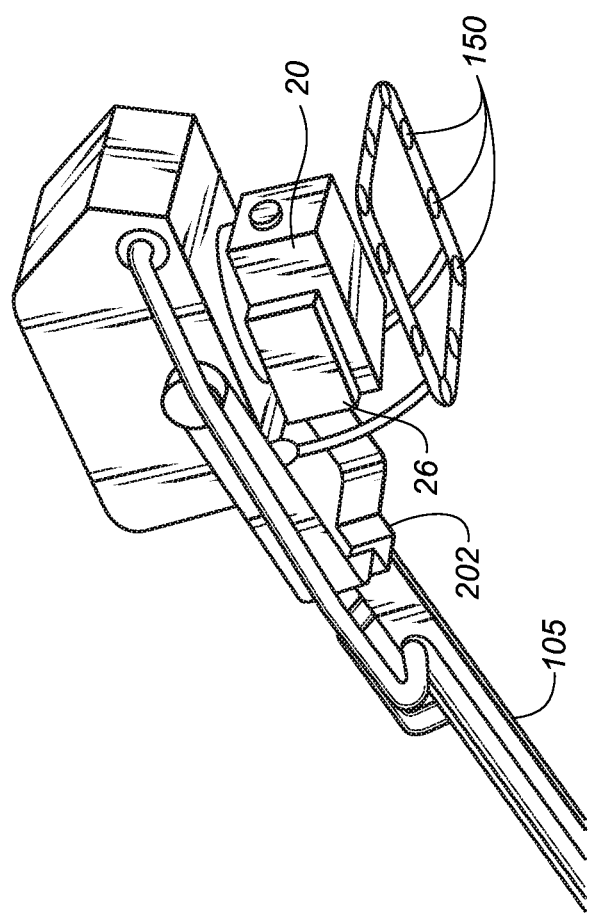
FIG. 2 illustrates an exemplary tube head assembly.

In certain exemplary embodiments of mobile radiography units that can provide a tomosynthesis capability, a moveable mounted x-ray source can, in addition, be supplied with a plurality of multiple individually controlled x-rays sources, e.g., a distributed x-ray source array such as CNT based x-ray sources 150. FIGS. 1 and 4 shows embodiments of a mobile tomosynthesis system where multiple individually controlled x-rays sources 150 comprise distributed x-ray sources (e.g., linearly distributed in the exemplary embodiment of FIG. 1). While illustrated as a mobile system, the x-ray source assembly 20 may be used in a stationary radiographic facility. As shown in FIG. 2, an x-ray source assembly 20 can include a plurality of distributed x-ray sources 150 arrayed in a prescribed spatial relationship. The distributed sources may be lower power x-ray sources, such as from 60 kVp to 120 kVp, and lower maximum mA output, such as from 1 mA to 100 mA. The x-ray source assemblies 20 can use a collimator to form beams that are directed toward a detector and patient P. The x-ray source assembly 20 may also include positioning, such as motors, which allow for directing the beam towards the detector and patient P. The moveable transport frame 920 can include a first display 910, and a second display may be disposed on the support arm 105 which may be used to control movement of at least the x-ray source assembly 20. Further, the system controller 915 can coordinate operations of the x-ray source assembly 20, the detector, and moveable transport frame 920 (e.g., via operator actions using the first display 910). The system controller 915 can control operations of the x-ray source assembly, which may include the collimator, positioning devices and triggering of image acquisition by emission of x-rays from the sources. For example, the system controller 915 can control x-ray emission for CT imaging procedures and/or for general radiography imaging procedures. The system controller 915 also can control operations of the detector, which may include triggering of the image acquisition and transmission of the acquired images back to the controller. In addition, the system controller 915 can control the movement of the transport frame 920.

Figure 3:
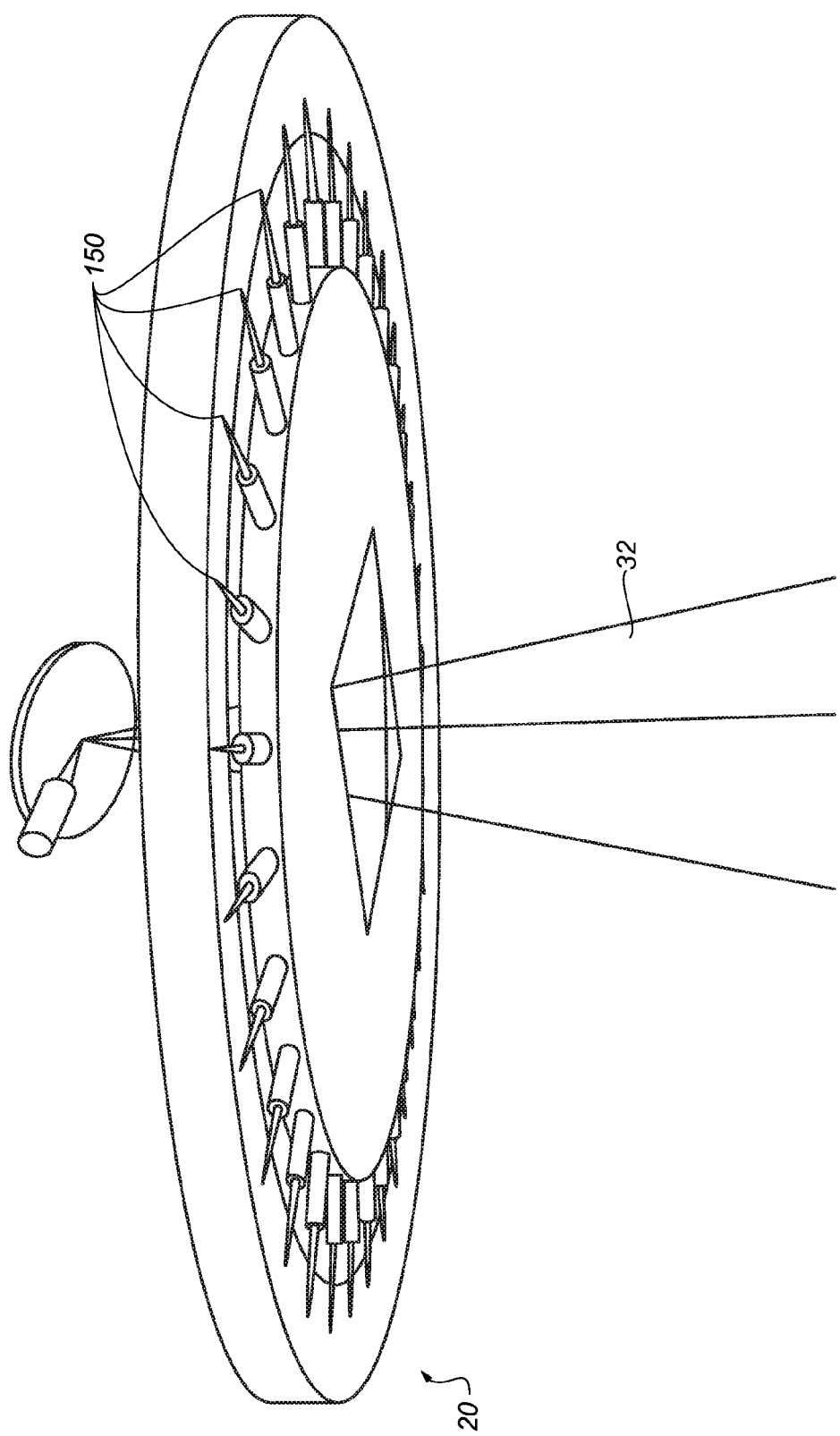
FIG. 3 illustrates another exemplary tube head assembly.
Figure 5:
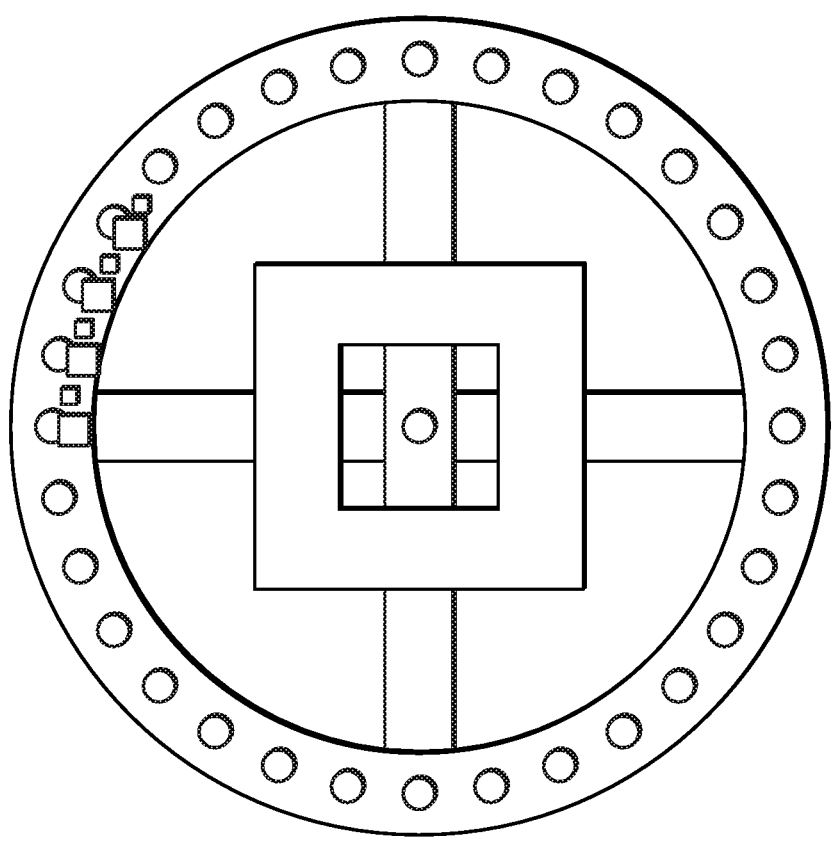
FIG. 5 illustrates another view of the tube head assembly of FIG. 3.

FIGS. 3-4 are diagrams that show an exemplary x-ray source assemblies 20 that can include multiple radiographic x-ray sources 150. As shown in FIGS. 3-4, an x-ray source assembly 20 of a mobile or stationary radiographic imaging system can include a first radiographic x-ray source 404 and collimator 402 as described herein, and second x-ray sources 150 comprising distributed sources (e.g., in a circular formation) that can be individually adjusted (e.g., collimated, see FIG. 5) and either permanently or temporarily attached (e.g., detachable). As shown in FIGS. 3-4, in one embodiment, a first radiographic x-ray source assembly 20 may include a central source 404 and a plurality of distributed x-ray sources 150 around a periphery of the central source 404 where at least the central source of the distributed x-ray sources has full (e.g., standard) x-ray power. The central source can have a wide range of kVp settings, such as from 50 kVp to 150 kVp, and high maximum mA output, such as from 10 mA to 400 mA, in order to accommodate many different exam types for general radiography. The central radiographic x-ray source 404 may be positioned at a center of the distributed array of x-ray sources 150. In one embodiment, the central radiographic x-ray source 404 may be a mobile/portable or stationary x-ray source/tube and of a different type of x-ray source than a distributed array of lower power CNT x-ray sources 150.

Other exemplary x-ray source assemblies may include multiple radiographic x-ray sources. In these embodiments an x-ray source assembly 20 may include a directed first radiographic x-ray source and second x-ray sources comprising a distributed source attachment (e.g., linear or other distribution) that can be either permanently or temporarily attached (detachable). The first radiographic x-ray source can be positioned at a center or other location in relation to the array of distributed sources. In one embodiment, the plurality of distributed x-ray sources can be mounted along a support bar (FIG. 1) that may be linear, circular, or other geometric shape. In one embodiment, the plurality of distributed x-ray sources can have a prescribed spatial relationship, where the prescribed spatial relationship is one or more linear tracks, 2D tracks, curves, polygons, rectangles or 3D paths. In one embodiment, collimated distributed sources may be attached to a curved support arm to maintain a single distance from a corresponding point on a DR detector panel. Exemplary distributed source attachments may have a first position for use and a second position for storage (e.g., folded) when not in use.

The x-ray sources can be, for example, a distributed array of field-emission based X-ray sources, such as sources having CNT cathodes. The X-ray sources may be stationary or relatively fixed in position with respect to each other within the array; the array itself may move as a single unit. This type of x-ray source may be capable of rapid on/off switching on the order of microseconds. Other suitable x-ray sources may include paired or pulsed conventional fluorocapable thermionic sources that are spatially separated. These options provide sufficient x-ray fluence with short exposure times and allow exposure sequences without overheating.

Figure 7:
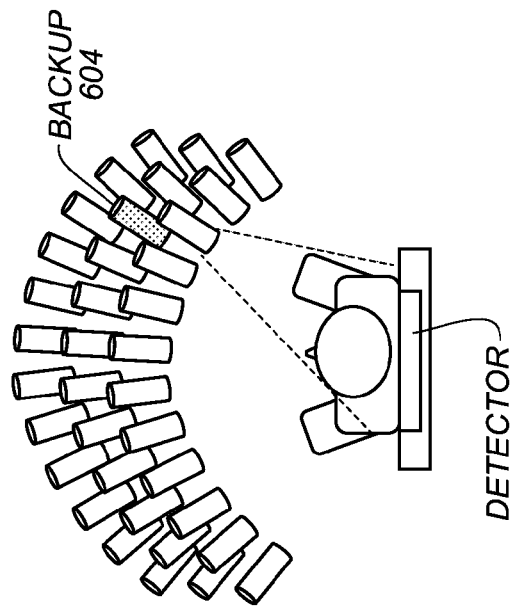
FIGS. 6-7 illustrate an arcuate assembly of selectable subsets of x-ray sources.
Figure 6:
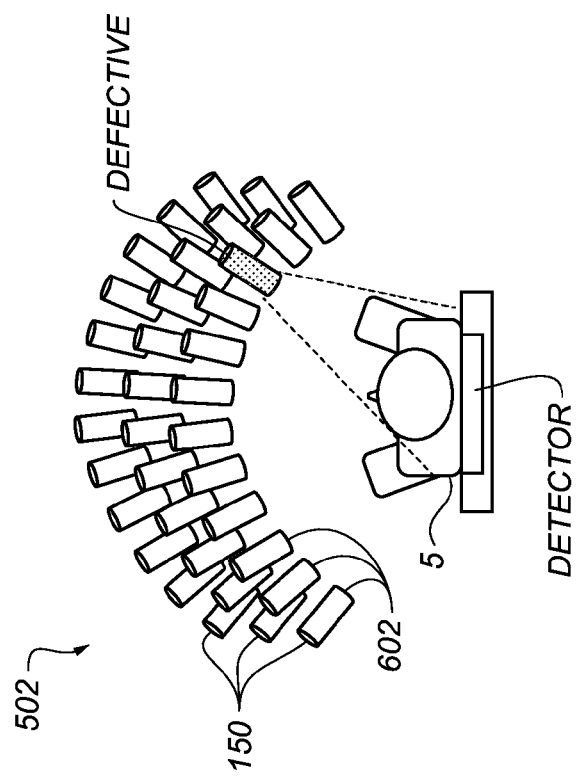

Referring to FIGS. 6-7, source array 20 is shown in an arcuate arrangement. Collimators for individual sources are not shown in FIGS. 6-7, but may be provided. Individual sources 602, for example, may be designated as a member of a first (primary) subset of sources that may be used until its performance degrades, or otherwise becomes unusable. Sources 604 may be designated as a backup source to primary sources 602 and becomes activated for use while source 602 is designated as deactivated or defective until it is replaced. After replacement, source 602 may again become designated as the primary source or may be designated as a backup to source 604. Primary and/or backup status of the sources in the array may be stored electronically and modified as needed, either automatically under program control, or via operator command. Activation of primary and/or backup sources may take place under automatic program control.

FIGS. 6-7 illustrate an array 502 of x-ray sources having several rows of sources extending along an arcuate dome above a subject 5. Here, a first row of the sources, including source 602, for example, may be designated as a primary subset of active x-ray sources, while the second row of sources, including source 604, may be designated as backups to the first row. Further, a third row of sources may be designated as additional backups to the second row of backup sources. Since these designations are arbitrary, any set of x-ray sources may be designated as primary and backup in various combinations, which designations may be electronically stored and accessed as necessary under program control. Operation of the x-ray sources and detector may proceed such as by energizing, or pulsing, an x-ray source and acquiring image data using a detector. A second exposure may be obtained by energizing another source to acquire second image data at the detector, and so on. Any number of images may be captured using controlled activation of the distributed array of x-ray sources, such as for tomosynthesis applications or individual projection images.

Figure 8:
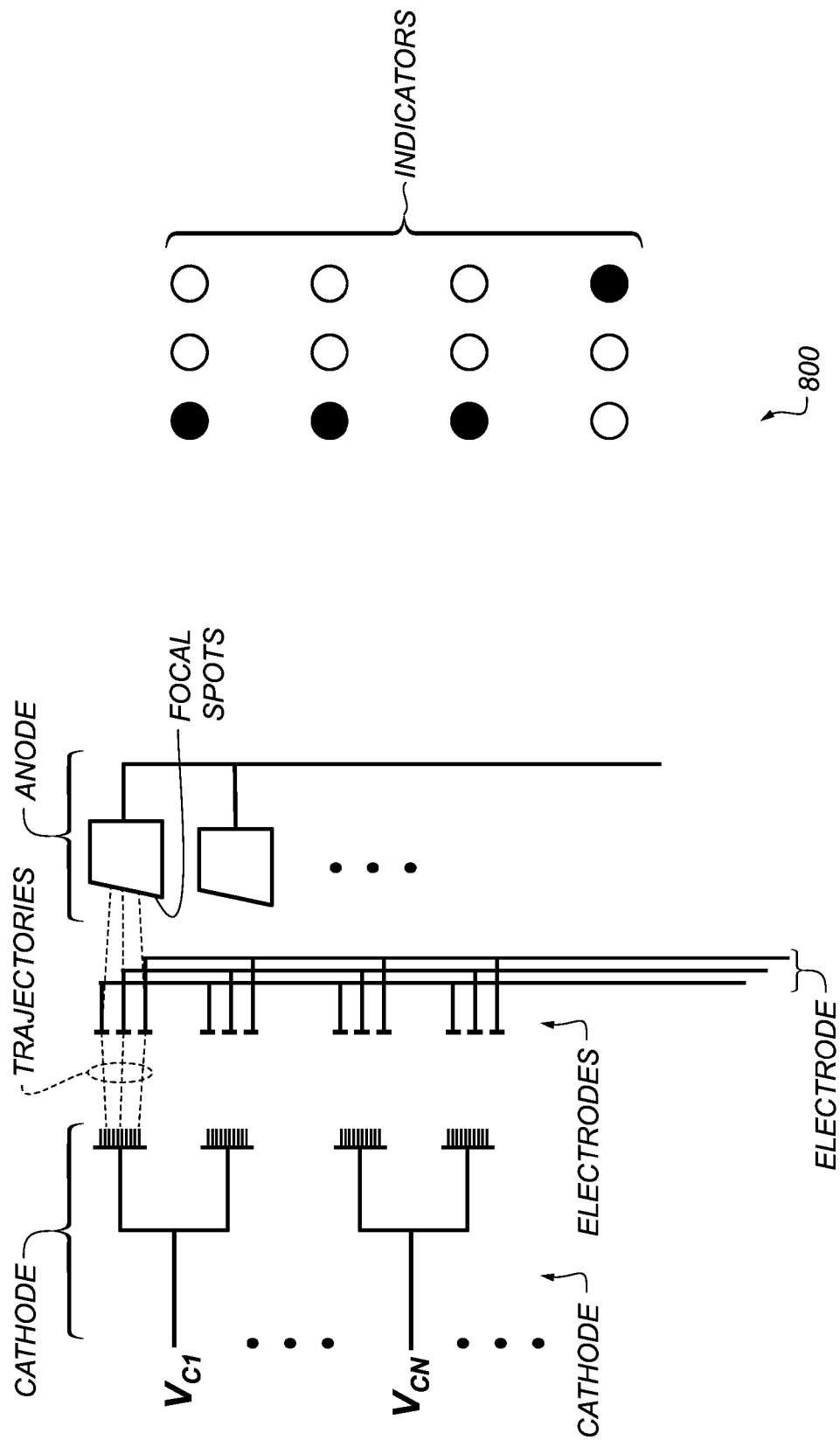
FIG. 8 illustrates an x-ray source selection circuit.

An exemplary x-ray source selection circuit is illustrated in FIG. 8. On the cathode side of the selectable x-ray source system 800 are several electron sources that may be activated by application of a negative voltage $V_{C1}-V_{CN}$ from a suitable voltage source. An electrode select circuit may selectively energize electrodes, one from each set of three, which accelerate the electrons generated by the cathode electron sources toward a corresponding anode which emits x-rays upon impact from the accelerated electrons. Because the electrodes are spatially separated, the electrons will be accelerated along a different trajectory depending upon which one of the three electrodes is activated. Each electron trajectory will impact a different focal spot on the anode. If a particular focal spot becomes defective over time, the corresponding electrode may be deselected and a second electrode from the set of three may be activated which alters the electron trajectory slightly so that the stream of emitted electrons impacts a different focal spot on the anode. Typically, an electrode may be activated by connecting it to a ground voltage because the voltages $V_{C1}-V_{CN}$ are connected to a negative voltage source. An electrode may be deselected by applying a negative voltage thereto, which does not cause electron acceleration as the voltage potential difference in the cathode is deactivated. Thus, different focal spots of the anode may be selected as back-up focal spots to avoid focal spots that have reached end of use. A set of visible indicators may be electrically connected to the electrode select circuit to indicate to an operator which of the electrodes are in use and/or which have reached end-of life.

In one embodiment, the arrangement or distribution 502 of low power x-ray sources 502 can be an array of CNT based x-ray sources. In one embodiment, a plurality or all of the electron beams emitted by the CNT sources, which may be arranged in a substantially circular formation in this example, may be directed at a single, shared anode. This anode embodiment may be a rotatable disc. For example, the anode embodiment may have a beveled edge so the electron beam can impinge the anode embodiment at the correct angle for x-ray emission. The anode embodiment (e.g., disk) may rotate so the points where the electron beams impact the anode are spread over a larger surface area of the rotating anode to reduce damage (e.g., overheating, melting).

As disclosed herein, embodiments of the invention may include an x-ray source assembly, such as a tube head, and may include a plurality of carbon nanotube based radiation sources configured to emit x-rays when energized, and a control circuit connected to the radiation sources to selectively energize a subset of the radiation sources. The control circuit may operate to selectively enable a first subset of the radiation sources to be powered while a backup subset are unpowered until they are designated as active x-ray sources. The designation as to primary or back-up x-ray sources may be stored electronically in a table and accessed to controllably power the primary x-ray sources as necessary.

Certain exemplary embodiments shown in the figures illustrate a central x-ray source with a conventional x-ray tube. This central x-ray source can be used to capture traditional x-ray images. On one embodiment, the distributed sources may be used to capture multiple projection x-ray images that can be processed to obtain a tomosynthesis dataset of images which may be used to reconstruct a 3D image of the subject (e.g., by applying reconstruction processing to the data). If a projection image of the subject is desired, the 3D reconstructed image may be used to generate 2D image without requiring an additional exposure of the subject to obtain the 2D projection image. Typically, the energy required for a single 2D projection image is higher than an individual image generated in a tomosynthesis scan. Thus, when a projection image of a subject is desired, the higher energy x-ray source is typically used to obtain the 2D projection image. However, the 3D reconstruction may obviate the need to obtain the higher energy exposure by extracting a 2D image from the stored 3D image.

As will be appreciated by one skilled in the art, aspects of the present invention may be embodied as a system, method, or computer program product. Accordingly, aspects of the present invention may take the form of an entirely hardware embodiment, an entirely software embodiment (including firmware, resident software, micro-code, etc.), or an embodiment combining software and hardware aspects that may all generally be referred to herein as a "service," "circuit," "circuitry," "module," and/or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

Program code and/or executable instructions embodied on a computer readable medium may be transmitted using any appropriate medium, including but not limited to wireless, wireline, optical fiber cable, RF, etc., or any suitable combination of the foregoing. The program code may execute entirely on the user's computer (device), partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer.

Computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified herein. The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified herein.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What it claimed is:

1. An x-ray tube head comprising:
   a plurality of cold cathode radiation sources for emitting x-rays when energized by an electric current; and
   an enabling circuit configured to selectively enable and disable any of a first subset of the cold cathode radiation sources to be switchably connected to a source of the electric current, and to selectively enable and disable any of a second redundant subset of the radiation sources to be switchably connected to the source of electric current;
   a detection circuit configured to detect whether any of the enabled radiation sources in the first subset is inoperable; and
   a switch circuit for switchably connecting selected ones of the enabled radiation sources in the second subset to the source of electric current.

2. The tube head of claim 1, wherein the enabling circuit is further configured to access electronic storage to identify a replacement radiation source.

3. The tube head of claim 2, wherein the enabling circuit is further configured to enable a selected one of the radiation sources in the second subset to be used as a replacement radiation source in place of the inoperable radiation source.

4. The tube head of claim 1, wherein the inoperable radiation source in the first subset has been previously associated with the enabled replacement radiation source in the second subset.

5. The tube head of claim 4, wherein the inoperable radiation source in the first subset has been previously electrically connected as a primary radiation source and the enabled replacement radiation source in the second subset has been previously electrically connected as a back-up radiation source.

6. The tube head of claim 1, wherein the enabled replacement radiation source in the second subset is positioned adjacent to its associated inoperable radiation source in the first subset.

7. The tube head of claim 6, wherein the plurality of radiation sources are logically divided into two or more subsets wherein selected ones of the subsets are electrically connected as primary radiation sources, and other selected ones of the subsets are electrically connected as back-up radiation sources.

8. An x-ray imaging system comprising:
   a source of x-ray radiation attached to a tube head at one end of a movable support arm, the support arm configured to be selectively positioned;
   a light source attached to the tube head and configured to move together with the movable support arm and the tube head, the light source further configured to visibly illuminate an area to be radiographically exposed by the imaging system, wherein the illuminated area coincides with a size of an area to be exposed to x-rays from the source of x-ray radiation; and
   a source of electric power configured to provide electric power to the light source to visibly illuminate the area to be radiographically exposed by the imaging system, the source of electric power configured to automatically provide the electric power to the light source in response to an action performed by an operator to use a portion of the x-ray imaging system other than the light source.

9. The system of claim 8, further comprising a collimator attached to the source of x-ray radiation, and wherein the action performed by the operator comprises physically contacting knobs to adjust the collimator, wherein, in response to the operator physically contacting the knobs, the source of electric power automatically provides electric power to the light source.

10. The system of claim 8, wherein the action performed by the operator comprises disengaging a brake or lock that is used to constrain movement of the support arm or the tube head, wherein, in response to the brake disengaging, the source of electric power automatically provides electric power to the light source to visibly illuminate the area to be radiographically exposed by the imaging system.

11. The system of claim 8, wherein the action performed by the operator comprises grasping a handle on the tube head or on the support arm, wherein, in response to the operator grasping the handle on the tube head or on the support arm, the source of electric power automatically provides electric power to the light source to visibly illuminate the area to be radiographically exposed by the imaging system.

12. The system of claim 8, wherein the action performed by the operator comprises touching any portion of the support arm or tube head, including a button, knob, touch screen display, or a burn guard on the tube head or on the support arm, wherein, in response to the operator touching any portion of the support arm or the tube head, the source of electric power automatically provides electric power to the light source to visibly illuminate the area to be radiographically exposed by the imaging system.

13. The system of claim 8, wherein the action performed by the operator comprises approaching the imaging system or moving a part of the imaging system, wherein, in response to the operator approaching the imaging system or moving the part of the imaging system, the source of electric power automatically provides electric power to the light source to visibly illuminate the area to be radiographically exposed by the imaging system.

14. The system of claim 8, further comprising a detector, wherein the detector is selected from the group consisting of an infra-red movement detector set to detect movement within a short distance from the imaging system, an ultrasound detector set to detect an object in close proximity to the detector, a contact detector set to detect contact on a surface of the tube head or support arm, a motor control device to detect movement of a mechanical joint in the tube head or support arm, an electromagnetic proximity detector set to detect movement within a short distance from the imaging system, an accelerometer to detect movement of the tube head or support arm or another device such as a hand held switch used to activate the radiation source, and a Bluetooth transceiver to detect an operator in proximity to the detector who is carrying a complementary Bluetooth transceiver.

15. A projection x-ray imaging system comprising:
 a first plurality of enabled stationary x-ray sources, each fixed at a different angle with respect to a subject to be imaged, and each for emitting radiographic energy to be used for capturing a 2-D projection image of the subject at the corresponding different angle; and
 a second plurality of stationary x-ray sources redundant with respect to the first plurality of enabled stationary x-ray source, each stationary x-ray source fixed at a different angle with respect to a subject to be imaged, and each configured to be enabled in response to a detection circuit detecting that a corresponding one of the first plurality of x-ray sources is inoperable.

16. The system of claim 15, wherein the first and second pluralities of stationary x-ray sources comprise cold cathode based x-ray sources fixed in a geometric array.

17. The system of claim 16, wherein the processing system is configured to generate another 2-D projection image of the subject based on image data in the reconstructed 3-D image of the subject.

18. The system of claim 17, wherein said another 2-D projection image presents the subject at a same angle as one of the 2-D projection images of the subject but which contains additional image data obtained from another one or more of the 2-D projection images of the subject.

19. The system of claim 18, wherein the geometric array is arranged as a rectangle, a line, a circle, a two-dimensional array, a two-dimensional curved dome, another polygon, or a combination thereof.

20. The tube head of claim 1, wherein the enabling circuit is electrically associated with a replacement radiation source.

\* \* \* \* \*